United States Patent [19]

Obagi

[11] Patent Number: 4,874,361

[45] Date of Patent: Oct. 17, 1989

[54] METHOD FOR HEALING DAMAGED SKIN

[76] Inventor: Zein E. Obagi, 200 Surry Dr., Bonita, Calif. 92002

[21] Appl. No.: 947,085

[22] Filed: Dec. 29, 1986

[51] Int. Cl.$^4$ .............................................. A61N 1/30
[52] U.S. Cl. ...................................... 604/20; 128/395
[58] Field of Search .................. 604/20, 21; 128/1.1, 128/1.2, 395; 424/1.1

[56] References Cited

U.S. PATENT DOCUMENTS

| | | | |
|---|---|---|---|
| 3,973,001 | 8/1976 | Jaeger et al. | 424/101 |
| 4,072,639 | 2/1978 | Yamaguchi et al. | 430/531 |
| 4,202,323 | 5/1980 | Zweig et al. | 128/1.1 |
| 4,558,700 | 12/1985 | Mutzhos | 128/395 |

Primary Examiner—John D. Yasko
Attorney, Agent, or Firm—Brown, Martin, Haller & McClain

[57] ABSTRACT

A composition and method of using the same for treating human skin of all races for a wide variety of skin ailments, including acne, blemishing, aging, sun damage and cancerous lesions, and other problems associated with skin disorders. The method comprises applying to a region of damaged skin a composition of trichloroacetic acid, a surfactant having cell growth stimulatory properties, and an emulsifier. The ratio of the various ingredients can be varied to effect optimal treatment for a particular type of skin. For treatment of certain disorders, the effect of the composition is enhanced if the skin is irradiated with a suitable light source. The latter stimulates even skin regeneration.

Several days after treatment, the damaged area peels off, and a new layer of vibrant, evenly colored, healthy skin is apparent. The procedure can be repeated without adverse effects, although generally a single application is sufficient.

16 Claims, No Drawings

METHOD FOR HEALING DAMAGED SKIN

BACKGROUND OF THE INVENTION

Over the years, a variety of medical treatments have been developed to treat chronic skin problems, such as acne, sun damage, precancerous lesions, scars, pigmentation disorders, wrinkles, and the like. These can be classified as procedures and methods that either supplement or prevent the loss of nutrients needed for healthy skin, or that remove regions of damaged skin. The former category comprises a truly bewildering variety of skin creams, lotions and ointments that are generally available over-the-counter. These creams either act to prevent water loss from the skin, or to deliver nutrients into the dermal layers. Suitable examples of such creams can be found in U.S. Pat. Nos. 4,424,234 and 4,235,889. Also, medical creams and antibiotics are used to treat acne vulgaris, or other skin conditions, are known to those skilled in the art.

For the most part, only three methods are now in routine medical use for removing damaged skin. They all involve the application of particular chemicals. The first can be termed the trichloroacetic acid peel; the second, resorcinol or salcylic acid peel; and third, the chemical peel. All three are of limited use, because as they are generally restricted to fair skinned people, and can often cause severe complications.

The trichloroacetic acid peel involves the application of trichloroacetic acid to the damaged area, followed by a short reaction time to allow it to interact with the damaged skin. Several days later, the damaged area peels off. The limitation of this method in that it is generally not feasible for deep peel dark skinned people with significant pigmentation because it peels the skin unevenly, and thus leaves uneven pigmented skin. For that reason, only fair skinned people are peeled with trichloroacetic acid treatment. Blacks and other dark skin race groups are excluded.

The second peel process involves the use of either resorcinol or salcylic acid. The use of either of these chemicals is generally restricted to correcting superficial skin problems. They are further limited in that they often can cause skin irritation.

The third peel process, or chemical peel, also has numerous drawbacks. First, it involves the use of phenol. The latter is known to be toxic and is thought to be potentially carcinogenic. Thus, this method must be carried out in a hospital, or in a similar controlled setting. In addition, the method is very painful and often requires that the patient be given medication during its application. Further, while the procedure does peel the skin evenly, it nevertheless often leaves uneven pigmentation of varying skin shades, or total loss of color, and, moreover, does not lend itself to repeat application because of its severe nature.

In addition to the above-described three types of skin peels, there exist a myriad number of less useful materials and procedures. For example, short exposure to ultraviolet light, with UVA or UVB, is known to be beneficial for psoriasis, vitiligo and mycosis fungoides, and simultaneously causes tanning of the skin. None of these methods uses full spectrum sun lamps.

It should be apparent from the above description that there is a need for additional methods of treating chronic skin disorders, particularly a method that would be universally applicable to all races, that is easy to perform, and, if need be, can be repeated one or more times.

SUMMARY OF THE INVENTION

A novel composition and method is described that has hithertofor not been recognized as being useful for treating a wide variety of chronic skin problems, particularly, pigmentation disorders, acne, wrinkles, aging spots, and superficial precancerous skin spots, as well as other disorders. The composition can be used alone, or with brief exposure to a suitable light source.

Presently, virtually all these disorders are either untreatable or treatable with limited success. The procedure consists of applying to the skin a composition comprising trichloroacetic acid, a surfactant having cell growth stimulatory properties, and an emulsifier that enhances even application of the composition to the skin so as to ensure subsequent uniform exposure of the skin to the composition, as well as to facilate light treatment if the latter is used. In addition, anti-microbial agents or chemicals that prevent oxidation can be added to the composition.

Depending on the type of skin disorder, as well as the race of the patient, the concentrations of the three main ingredients, that is, trichloroacetic acid, surfactant and emulsifier, will vary. For light-skinned patients or for superficial skin problems, low concentrations of trichloroacetic acid will be utilized in the range of about 10%, while for dark-skinned patients, or if more severe treatment is required, concentrations up to approximately 50% will be employed.

For treatment of deep skin disorders the effect of the composition is enhanced if a short time after application of the composition, the skin is irradiated with a light source that generates ultraviolet, infrared, and full spectrum visible light. The light coacts with the composition thereby causing skin regeneration without tanning. Depending again on the severity of the skin disorder, exposure to the light source will be for either short or long durations of time. The latter generally will not exceed 15 minutes.

About three days following application of the composition and irradiation, the skin begins to peel, and the peeling process is essentially complete by the end of the tenth day. During this time, the cell growth stimulating agent effectively provides a vibrant new layer of skin to replace the damaged skin. The procedure can be used to treat virtually all parts of body skin and is not restricted, as are most other methods, to treatment of the face. Moreover, unlike other methods, the process described herein can be repeated as often as is needed as it does not irreversibly kill skin cells needed for future skin growth.

DETAILED DESCRIPTION OF THE INVENTION

A preferred embodiment of the instant invention consists of applying a composition to damaged areas of skin, followed by irradiating the area to effect a peeling and removal of the skin. Exposure to light acts to stimulate a total regeneration of the treated area and aids in correcting the damage. It should be noted that while the peeling process is enhanced by the application of light, that for superficial peels, the composition alone performs satisfactory.

The composition consists essentially of three ingredients. The first is an acidic substance, such as for example, trichloroacetic acid. The second is a surfactant having cell growth stimulatory activity, and the third is an emulsifier. By mixing trichloroacetic acid with the other two components, a special hithertofor unknown composition is formed which can be used to remove either deep or superficial or damaged skin. Ancillary materials and methods can be employed prior to, or after, treatment, with the composition alone, or the composition coupled with light exposure. These are not directly involved in affecting the skin peeling process. For example, regions of skin that are not the subject of treatment are protected from irradiation, such as the patient's eyes, lips, etc. The methods for protecting these areas are well known to those skilled in the art which consists of sunglasses, or cloth coverings, bandages, sunscreens, etc. In addition, prior to the application of the composition, the area to which it is applied can be cleaned with a suitable bacteriostatic agent.

While it is anticipated that a variety of acidic substances, in addition to trichloroacetic acid, may be useful in the subject invention, such as for example phenol, resorcinol, etc., trichloroacetic acid is preferred as it has been extensively tested in prior art peeling processes and found to be relatively safe for such treatments. Generally, the composition will contain from 10 to about 50% trichloroacetic acid. Determinative of the concentration is whether a patient needs a superficial or deep peel, as well as the patient's skin color. For superficial treatments, a concentration in the range of 10% will generally be adequate, while for more severe cases, higher concentrations of trichloroacetic acid are desirable. It will be apparent to those skilled in the art what the preferred concentration of trichloroacetic acid is for a particular application. For those treatments where the concentration of trichloroacetic acid is in doubt, however, patch testing a very small area of the patient's skin will indicate the concentration of trichloroacetic acid that should be employed. While the use of trichloroacetic acid in the peel process is not hazardous, if used alone, it may cause uneven peeling and thus yield uneven pigmented skin. Therefore, after extensive research novel surfactants and emulsifiers have been discovered that combine with the trichloroacetic acid to overcome these problems.

The second ingredient of the composition is a surfactant having cell growth stimulatory activity. The term surfactant is meant to encompass either a molecularly identified substance, or a mixture of particularly chemically characterized molecules having the described properties. A variety of suitable surfactants, either of plant or animal origin are now known to those skilled in the art. For example, epidermal growth factor, and fibroblast growth factor are two such molecules. We have found, however, that steroid saponins are preferred in the subject invention, particularly steroid saponins approved for use by the FDA having registry #121.1163. Generally, they will be used at a concentration of about 0.1%; however this concentration can vary depending on the need for a light or deep peel. The deeper the peel, the higher the concentration of the cell growth stimulatory molecules that will be utilized.

The third ingredient in the invention composition is an emulsifier. Emulsifiers are defined as those compounds which are pharmacologically and physiologically tolerated by the diseased skin surface, and which impart a favorable consistency to the compositions for their topical application to the skin, and moreover, which facilitate the taking up of the composition by absorption and/or resorption and/or persorption. A variety of emulsifiers can be used, particularly salts of aliphatic monocarboxylic acids with 10 to 22 carbon atoms, such as calcium stearate, magnesium stearate, aluminum stearate or zinc stearate. Also, emulsifier mixtures of mono- and/or diglycerides of aliphatic; monocarboxylic acids with 10 to 22 carbon atoms can be used, but these tend to reduce the activity of the trichloroacetic acid. However, we have determined that chlorhexidine gluconate works satisfactorily when it is in a solution containing isopropyl alcohol. A concentration in the a range of about 0.4% chlorhexidine gluconate is most effective. The emulsifier is employed to effect even spreading and absorption of the composition across and into the areas of damaged skin, and in this way ensures that upon subsequent irradiation, that the peeling of the damaged layer occurs uniformly. This in turn ensures that the new skin layer remaining after peeling does not exhibit light or dark patchy areas, rather the entire layer of skin is of uniform shading.

The composition of the instant invention can also contain small amounts of antioxidants to prevent oxidative destruction of those components of the composition susceptible thereto. Suitable antioxidants as well as their uses are described in "Antioxidants" in Volume 8 of *Ullmann's Encyclopedia of Technical Chemistry*, Fourth Edition. In addition, the composition may also contain small amounts of chemical preservatives to prevent or retard microbial degradation. Examples of useful preservatives are described on pages 440 to 461 in Volume 11, 1960, of *Ullmann's Encyclopedia of Technical Chemistry*, Third Edition. In general, the addition of about 0.01 to 0.2% by weight of preservative, relative to the weight of the total composition, suffices to prevent growth of molds, yeasts and bacteria.

Several properties of the cell growth stimulatory ingredient merit discussion. In addition to stimulating dermal cell growth, a further desirable property is its capacity to penetrate into the skin, thereby stimulating cell growth in the layers beneath those that are being removed during the peel process. While steroid saponins have been determined to have this skin penetrating property, and therefore is the preferred embodiment in the instant invention, it is to be anticipated that a variety of other cell growth stimulatory molecules can be combined with suitable skin penetrating agents, for example such as dimethyl sulfoxide, and hence be similarly employed. In addition, it is to be further anticipated that similar results can be realized by associating, via chemical coupling, sealing in lipid vesicles or other means, a surface active substance and a cell growth stimulatory compound. In this instance, the surface active property of the ingredient will not be intrinsic to the cell growth stimulatory property, but still be deliverable to the dermal layers.

An additional property associated with the use of steroid saponins is that they ameliorate skin irritation arising from ultraviolet light treatment. While this aspect of the surfactant ingredient is appealing, it is not requisite for satisfactory results.

From a wide variety of surfactants tested, we have found that the preferred surfactant is a steroid saponin, (Compound 272) produced and owned by Mikuda Company, Inc.

For certain treatments, after application of the composition to the damaged area of skin, it is treated with light that has both ultraviolet and infrared components. It is important to be aware that the purpose of light treatment is not to tan the skin, rather the light has a skin regenerating effect. Depending on the race of the individual, the duration of light treatment will vary. Any method for determining the sensitivity of a patient's skin to ultraviolet radiation may be used to first determine its sensitivity to a particular dose. These methods are well known to those skilled in the art, and consist of basically performing minimal erythema dose test for different time periods of exposure to determine the proper dose to be administered to a particular patient. By performing many such tests it is possible to construct a graph establishing the optional time of exposure for a particular skin type. Generally, times on the order of minutes will be utilized regardless of race.

By doing various tests, we have found that for the purposes of the instant invention the major skin types are: Type A—very blonde and fair skin; Type B—blonde with fair skin; Type C—light skin, able to tan, easily sunburned; Type D—dark skin, able to tan, rarely sunburned; and Type E—black skin, rarely sunburns. For these classes we have further found that the amount of radiation is approximately two minutes for Type A skin, three minutes for Type B skin, three and a half minutes for Type C skin, four minutes for Type D skin, and about five minutes for Type E skin. It will of course be obvious to those skilled in the art that these times are only approximate and can be varied.

In addition to skin coloration, other factors will also be determinative of the duration of radiation. If there is a need to perform a deep peel, then radiation treatment can be expected to be carried out for longer periods of time. This is necessary as the skin has on the order of 20 to 30 layers, and if the damaged area is many layers deep, then in order to effectively peel these layers, it is desirable to prolong the period of exposure to ultraviolet light.

A variety of lamps can be utilized as a source of ultraviolet radiation with which to irradiate the skin, provided that they generate ultraviolet radiation in the range of about 290–400 nanometers. In addition it is also preferred that these lamps generate infra-red (heat) radiation typical of the spectrum of such radiation produced naturally by the sun. A variety of suitable filters can be disposed between the lamp and the patients skin to control either the extent or intensity of exposure.

It is important to note that the lamps utilized in the instant invention are not tanning lamps. The lamps most effectively employed are those that burn or peel the skin but do not tan it. There are a wide variety of commercial lamps from which one can choose to practice the present invention. However, we have found that the Alpine Lamp, produced by Hanovia Corporation, is particularly useful. Additionally, examples of other useful lamps are the Blake-Ray Lamp produced by Ultraviolet Products, Inc. or the Burdic Lamp produced by Burdic Company, Ohio can also be employed. It is further desirable that the lamp be readily portable. This facilitates practicing the invention in a doctor's office.

As described above, the dose of ultraviolet radiation is a function of the race of the patient being treated, as well as the severity of skin damage. It is anticipated that for most applications, the Alpine Lamp (Hanovia) will be located about 12 to 24 inches from the patient's skin and the skin irradiated for a time in the range of about 2–15 minutes. Generally, a dark skinned patient will require longer irradiation time than a fair skinned patient. It is worth noting that if suitable empirical tests are performed to precisely determine the dose of ultraviolet light needed, that irradiation need be performed only once. However, it will be appreciated that the nature of the invention lends itself to multiple applications if this should be desired.

A key feature of the instant invention alluded to above is that it is applicable for treating skin of different races. It is particularly advantageously utilized to peel dark skin which has a tendency to produce uneven, nonuniform skin shading. The invention can also be used with great success to treat Oriental skin.

After application of the composition, with or without subsequent irradiation, a variety of washing and cleansing procedures can be employed to remove the composition. Subsequent care of the skin is minimal and generally consists of merely washing with any number of commercially available soap formulations. After about three days post-irradiation, noticeable peeling will occur, and this should be complete at about 10 days post-irradiation. During this time, the patient can employ standard facial hygenic washing procedures, and in some instances, it may be desirable to apply a topical cream containing a suitable antibiotics should it appear that there is a risk of dermal infection. Further ancillary methods to aid the peeling process, but which are not necessary for its realization, is the application of a suitable benzoyl peroxide cream, or retinoic acid, which enhance cell regeneration to the treated area. The latter enhances the peeling process and contributes to the overall appearance of the new skin layer. At later times during the peeling process, a variety of moisturizing creams can be favorably applied to the patient's skin to reduce any redness, or chapness that may appear.

It will be understood by those skilled in the art that the following examples are mere representations of several readily conceivable formulations of the methods utilized to realize the instant invention. Thus, they are provided by way of illustration and not limitation.

EXAMPLE I

Preparation of Surfactant Cell Growth Stimulatory Ingredient

An organic extract of the yucca plant was prepared using standard synthetic organic chemistry techniques, which yielded a steroid saponin fraction. The fraction is slightly hydroscopic, and yields a clear solution at a 10% concentration in water. Moreover, a 20% solution has a pH of approximately 4.5, and a density of about 375 gms/per liter. The steroid saponin fraction is slightly hydroscopic, water soluble, and insoluble in benzene and ether. The material is approved for use by the United States government under Federal Registration number paragraph 121.1163.

EXAMPLE II

The face of a 20 year old female suffering from acute acne vulgaris was washed with suitable antibacterial cleansing agents, and then a composition consisting of 10% trichloroacetic acid, 0.1% cell growth stimulatory agent as described in Example I, and 0.4% chlorhexidine gluconate, was applied to the damaged areas. Areas of the skin were covered with suitably fashioned cloth to protect it from unnecessary ultraviolet light damage, and then the patient placed a distance of 12 inches from the light source. A Burdic K lamp (Hanovia) was utilized, and the patient's face was irradiated for a period of 5 minutes. Next, following irradiation, the patient's skin was cleansed to remove the composition, and washed with a mild soap solution. Three days after returning home, significant peeling was apparent upon a routine check-up, and by ten days, the peeling process was complete. A second treatment done one month after the first treatment was milder and the composition alone was used.

EXAMPLE III

Treatment of a Dark Skinned Patient

A composition having approximately 30% trichloroacetic acid, 0.1% compound 272 as described in Example I, and 0.4% chlorhexidine gluconate, was applied to the skin of a 45 year old negroid female with severe facial acne, scars, and pigmentary problems. Those areas of the skin that were not the subject of treatment were shielded from exposure to ultraviolet light, and then the face irradiated at a distance of 1½ feet, for 12 minutes utilizing a Burdic K Lamp as described in Example II. Similar to the results seen in the preceding Example, after three days post treatment peeling was apparent, and was substantially complete by 10 days. Three treatments were needed, one with light and two without.

EXAMPLE IV

Treatment of Dark Skinned Patients With Severe Pigmentary Complications

A 44 year old female negroid patient suffering from severe acne scarring, and congenital skin problem associated with sebaeous gland hyperplasia was treated as described in the above examples with the following modifications. Trichloroacetic acid was used at a concentration of 50%, and 5 treatments were performed, one with light and four without. Light exposure was for 12 minutes. Marked improvement in the patients facial appearance was apparent after the first treatment, and was complete by the end of the fifth treatment.

EXAMPLE V

Peel Process Applied to Sun Damaged White Skin

A composition containing approximately 50% trichloroacetic acid, 0.1% compound 272 obtained from Mikuda Corp., and an emulsifier, chlorhexidine gluconate, was applied to the face of a 70 year old caucasian male exhibiting severely sun damaged skin. Because of the severe skin damage, a slightly higher amount of trichloroacetic acid was used when compared to the patient treated in Example II. The remaining treatment was similar to that described in Examples II and III, except that only one treatment with light was needed. Ten days post treatment the patient revealed new skin clearly lacking the sun damaged regions.

EXAMPLE VI

Removal of Wrinkles

A white 68 year old man was treated as described in the above examples excepting that the composition had 50% trichloroacetic acid, and the patient was exposed to light for 6 minutes. Two treatments were performed, one with light, the other without. Virtually all wrinkles were removed several weeks post treatment.

EXAMPLE VII

Treatment of Oriental Skin

A 60 year old Chinese female with age spots (lentigo senilis), and displays sun damage and wrinkles on the face was treated as follows. A composition as described in Example III was applied to the face, and the patient irradiated with light generated from an Burdic K (Hanovia) for about 8 minutes. After radiation treatment the face were washed with a mild soap solution. Three days post treatment peeling was apparent, and complete by the end of ten days.

EXAMPLE VIII

Treatment of Actenic Keratosis (precancerous lesions) and Lentigos

A white skinned 52 year old male was treated as described in Example V with the following changes. 30% trichloroacetic acid was used, and a single exposure to light for 8 minutes was employed. Nearly complete elimination of the skin disorder was achieved.

EXAMPLE IX

Removal of Precancerous Lesions from Oriental Skin

A 64 year old Chinese female was treated to remove precancerous lesions using the materials and methods as described above. The composition consisted of 50% trichloroacetic acid, and treatment was effected 2 times, once with light and once without. Light exposure was for 10 minutes. Ten days post treatment there was a marked reduction in the severity and number of wrinkles.

EXAMPLE X

Treatment of Hispanic Skin Suffering From Improper Phenol Peel

A 62 year old Hispanic female suffering from severe pigmentation problems caused by a prior phenol peel was treated by the method of the instant invention using the materials and methods described in the preceding examples with the following exceptions. Approximately 30% trichloroacetic acid was utilized in the composition, and the duration of light exposure was 12 minutes. Additionally, a total of 4 treatments were formed, one with light alone, and three with the composition alone.

It will be apparent to those that are skilled in the art that there are a variety of substitutions that can be made to the materials and methods described above without deviating from the intended purpose of this instant invention. Thus, it is intended that the instant invention is not to be construed as being limited to the presented examples, and is only limited by the scope of the appended claims.

I claim:

1. A method of treating damaged areas of skin comprising the steps of:
    applying to said damaged area a therapeutically effective amount of a composition comprising trichloroacetic acid, a surfactant having growth stimulatory activity, and an emulsifier; and
    irradiating said area of damaged skin in contact with said composition for a time sufficient to induce peeling of said damaged area.

2. A method as described in claim 1 wherein said composition comprises about 10–50% trichloroacetic acid, and 0.1% surfactant having growth stimulatory activity.

3. A method as described in claim 2 wherein said growth stimulatory agent is a steroid saponin.

4. A method as described in claim 3 wherein said steroid saponin is registered with the Federal government and has Federal registration no. 121-1163.

5. A method as described in claim 6 wherein said emulsifier is chlorhexidine gluconate.

6. A method as described in claim 1 wherein said emulsifier is selected from the group consisting of salts and mono- and diglycerides of aliphatic monocarboxylic acids having 10-22 carbon atoms.

7. A method as described in claim 1 wherein irradiation of damaged skin comprises lights of wavelengths from about 290-400 nanometers, visible light and infrared light.

8. A method as described in claim 1 wherein said damaged skin is selected from the group consisting of seborrheic keratosis, acne rosaua, lentigo senilis, and acne vulgaris, meloma, actenic veratosis, and scars.

9. A method of treating damaged areas of skin comprising the steps of:
   testing the skin to determine its sensitivity to light radiation;
   shielding non-damaged areas of skin from said radiation;
   applying to said damaged area a therapeutically effective amount of a composition comprising trichloroacetic acid, a surfactant having cell growth stimulatory activity, and an emulsifier; and
   radiating the damaged area of skin having said composition for a time sufficient to induce peeling of said skin based on its sensitivity to said radiation.

10. A method as described according to claim 9 wherein said composition comprises about 10-50% trichloroacetic acid.

11. A method as described in claim 10 wherein said surfactant having growth stimulatory activity is a steroid saponin.

12. A method as described in claim 11 wherein said steroid saponin has Federal Registry No. 121-1163.

13. A method as described in claim 12 wherein said composition comprises 0.1% surfactant.

14. A method as described in claim 13 wherein said light radiation comprises light in the region of about 290-400 nanometers, visible and infrared light.

15. A method for treating skin disorders comprising applying to a region of skin a therapeutically effective amount of a composition comprising between about 10-50% trichloroacetic acid, 0.1% steroid saponin, and an emulsifier for a time sufficient to induce peeling of said skin.

16. A method as described in claim 15 wherein said emulsifier is chlorhexidine gluconate.

* * * * *

UNITED STATES PATENT AND TRADEMARK OFFICE
CERTIFICATE OF CORRECTION

PATENT NO.   :   4,874,361
DATED        :   October 17, 1989
INVENTOR(S)  :   Obagi, et al It is certified that error appears in the above-identified patent and that said Letters Patent is hereby corrected as shown below:

On the title page item (76) should read --

Zein E. Obagi and
George H. Michel ---.

Signed and Sealed this

Twenty-eighth Day of April, 1992

Attest:

HARRY F. MANBECK, JR.

*Attesting Officer*         *Commissioner of Patents and Trademarks*